(12) United States Patent
Norman

(10) Patent No.: US 9,833,602 B2
(45) Date of Patent: Dec. 5, 2017

(54) TATTOO DEVICE WITH INTERCHANGEABLE COLORS

(71) Applicant: Joyce Leigh Norman, Worthington Springs, FL (US)

(72) Inventor: Joyce Leigh Norman, Worthington Springs, FL (US)

(*) Notice: Subject to any disclaimer, the term of this patent is extended or adjusted under 35 U.S.C. 154(b) by 231 days.

(21) Appl. No.: 14/702,260

(22) Filed: May 1, 2015

(65) Prior Publication Data

US 2016/0074646 A1    Mar. 17, 2016

Related U.S. Application Data

(60) Provisional application No. 62/050,092, filed on Sep. 13, 2014.

(51) Int. Cl.
  *A61B 17/34* (2006.01)
  *A61M 37/00* (2006.01)

(52) U.S. Cl.
  CPC .... *A61M 37/0084* (2013.01); *A61M 37/0076* (2013.01)

(58) Field of Classification Search
  CPC .... A61B 17/34; A61B 17/3417; A61M 37/00; A61M 37/0084; A61M 37/0076
  See application file for complete search history.

(56) References Cited

U.S. PATENT DOCUMENTS

| 4,798,582 A | 1/1989 | Sarath et al. |
|---|---|---|
| 5,054,339 A | 10/1991 | Yacowitz |
| 6,505,530 B2 | 1/2003 | Adler et al. |
| 6,626,927 B1 | 9/2003 | Koplen |
| 7,922,688 B2 | 4/2011 | Bodduluri et al. |
| 2007/0191736 A1* | 8/2007 | Alden ............... A61B 5/15146 600/583 |
| 2010/0280312 A1* | 11/2010 | D'Alessio ........ A61B 17/00491 600/104 |
| 2013/0226211 A1 | 8/2013 | Xiao |
| 2014/0094837 A1 | 4/2014 | Danenberg |
| 2014/0236169 A1 | 8/2014 | Imran |
| 2014/0271897 A1 | 9/2014 | Pathak |

FOREIGN PATENT DOCUMENTS

| EP | 2206530 A1 | 7/2010 |
|---|---|---|
| WO | WO 2009091596 A1 | 7/2009 |
| WO | WO 2014086342 A3 | 8/2014 |

* cited by examiner

*Primary Examiner* — Victor Nguyen
(74) *Attorney, Agent, or Firm* — Lisa Foundation Patent Law Clinic at Arizona State University

(57) ABSTRACT

This invention provides novel apparatus' and methods for tattooing skin. One embodiment provides an apparatus for tattooing skin comprising a frame and a plurality of pressurized compartments for storing tattooing fluids. A user may select one or more of the pressurized compartments to dispense a chosen skin colorant contained in the compartment(s). A fluid dispenser receives the chosen skin colorant(s). The tattooing fluid(s) in the chosen pressurized compartment(s) is forced into the fluid dispenser by a pressure source in the pressurized compartment, and by a pumping mechanism coupled to the apparatus. Tattooing fluid is provided to a tattooing needle through a fluid connection coupled to the fluid dispenser and disposed at an operating end of the tattooing needle.

7 Claims, 6 Drawing Sheets

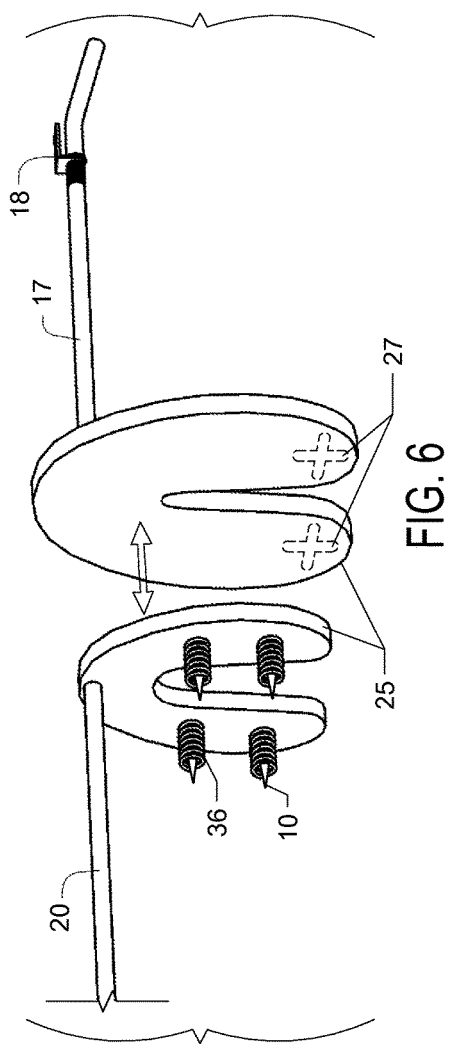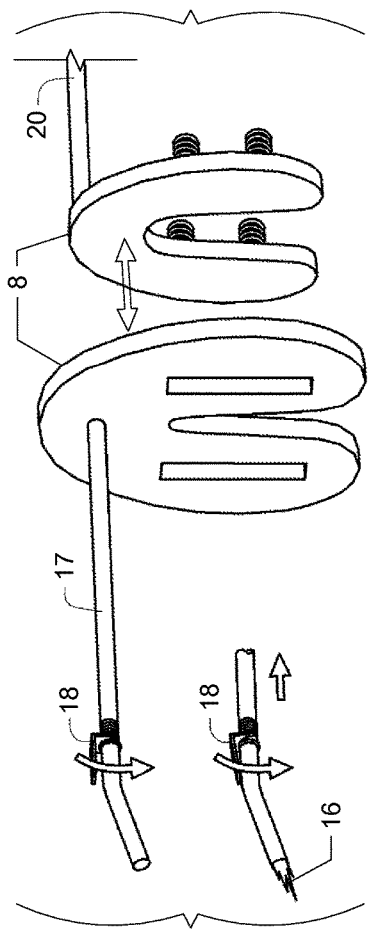

TATTOO DEVICE WITH INTERCHANGEABLE COLORS

CROSS REFERENCE TO RELATED APPLICATION

This application claims the benefit of the provisional application filed by inventor Joyce Norman on Sep. 13, 2014. The application number of the provisional application is 62/050,092. This utility application claims the benefit of the provisional application under 35 U.S.C. 119(e).

BACKGROUND OF THE INVENTION

1. Field of the Invention

The present invention generally relates to a device and a method for tattooing or applying permanent makeup to a patient or customer (used interchangeably through the application). More particularly, the invention relates to a tattooing device and a method of using the device which is equipped with multiple user-selectable compartments filled with fluids for tattooing, a fluid dispenser, an assembly of fluid pathways, a tattooing needle and an adjustable tip.

2. Description of Related Art

The practice of tattooing or applying permanent make-up requires the use of a sharp needle or cluster of needles to input ink into the skin of a patient. Usually, the needle is dipped into an ink reservoir throughout the tattooing process to supply pigment to the needle. The needle repeatedly punctures the patient's skin through a reciprocating motion. The tattooing device is a unit that houses the needle and includes a mechanism for reciprocating the needle. The practice of repeatedly dipping the needle into an ink reservoir is inconvenient and time consuming. Moreover, the process undermines the sterility of the pigment because dust, bodily fluids from other patients, or other harmful substances may enter the open reservoir of ink. It also undermines the tattoo artist's ability to get into an artistic flow because he or she must continually stop to dip the needle. Similarly, because many tattoos involve multiple colors, a tattoo artist must clean or change needles and fill a new reservoir when he or she wishes to use a different color.

Maintaining a high standard of hygienic handling in the tattooing industry is essential to avoiding the transmission of highly infectious diseases, such as HIV and hepatitis, from one patient to another. The tattooing procedure may draw blood, blood serum, or other bodily fluids. The parts of a tattooing device that directly contact a customer are likely to be contaminated by the patient's bodily fluids. The parts in direct contact with a patient must therefore be sterile prior to treatment. Typically, the parts of a tattooing device that directly contact a patient, such as needles, are disposed of after use on a patient. The parts that are reused must be thoroughly cleaned and sterilized after each use. This requires substantial time, energy and money. It also requires extreme care by tattoo artists to ensure that the process is completed correctly and thoroughly.

Some tattoo devices attempt to solve the foregoing problems by providing an ink reservoir integrated with the device. Others couple a source of tattooing ink to the tattoo needle and attempt to maintain a constant and controllable amount of ink to the needle. To overcome hygienic problems, some devices divide the parts into modules. One module may consist of parts that may be exposed to potentially infectious substances and another consists of parts that do not come into contact with infectious substances. The former module is disposed after each use and replaced.

In order to reduce the complexity and length of the Detailed Specification, and to fully establish the state of the art in certain areas of technology, Applicant herein expressly incorporates by reference all of the following materials identified in each numbered paragraph below.

U.S. Pat. No. 4,798,582 describes a needle cartridge with a reservoir filled with pigment that discharges ink to the tattooing needle assembly through a ball valve.

U.S. Pat. No. 5,054,339 describes a source of tattooing ink coupled to the tattoo needle unit in order to constantly and controllably provide ink during the tattooing procedure.

U.S. Pat. No. 6,505,530 describes a more hygienic tattooing device with a disposable module and an optional ink module attached to the device.

U.S. Pat. No. 7,922,688 describes a plurality of reservoirs containing a therapeutic or cosmetic substance. A delivery device may be selectively coupled to a reservoir, and delivery of the substance may be achieved by a pressurization source.

WO 2009091596 describes a writing pen with a writing tip for dispensing a user selectable variable color ink from an internal mixing chamber.

U.S. Pub. No. 2014/0271897 describes an injection apparatus with a built-in pigment reservoir that controllably releases pigment to the needle via a control valve.

U.S. Pub. No. 2014/0236169 describes a device with multiple compartments for delivery of different colorants and/or combinations of colorants. Each compartment of the invention may be coupled to the applicator by means of a control valve to allow a user to switch and combine colorants.

WO 2014086342 describes a tattooing device with an ink reservoir comprising a plurality of different color compartments routed by individual color lines to the needle.

Some of the above mentioned devices are constrained to supplying a single color. Others are difficult to clean, sterilize and prepare for the next customer. Many of the devices are unwieldy and cumbersome. Additionally, the weight is unevenly distributed in many of the devices, making them even more difficult and awkward to use. Some attempt to solve the problem of controlling the amount of ink provided to the needle, but do so ineffectively. None of the devices provide a safe, convenient, and quick way to change between colors during the application of a tattoo.

In view of the above related art, there remains a need for a tattooing device which is capable of efficiently applying multiple colors in one tattoo operation without the need for time consuming procedures.

Applicant believes the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Applicant will amend the specification to expressly recite the essential material that is incorporated by reference as allowed by the applicable rules.

SUMMARY

The present invention provides, among other things, a tattooing device configured to apply multiple colors as selected by a tattoo artist in one tattoo operation without the need for time consuming and cumbersome procedures. The device is easy to clean and prepare for the next patient.

Moreover, the device evenly distributes the weight and includes interchangeable barrels to accommodate various preferences of tattoo artists.

The invention comprises a tattooing apparatus comprising a frame with an operating end and a distal end adapted to receive a motor. A reciprocating armature is coupled to the motor and a tattooing needle is coupled to the reciprocating armature. The tattooing needle comprises an operating end that extends beyond the operating end of the frame. The tattooing apparatus further comprises a fluid dispenser, a fluid connection coupled to the fluid dispenser and disposed near the operating end of the tattooing needle. In addition, the tattooing apparatus comprises a plurality of piercing tubes each coupled to the fluid dispenser and a plurality of pressurized compartments comprising: a first end disposed adjacent to a piercing tube and comprising a self-sealing fluid-tight seal, a second end configured to be selected, and a reservoir coupled between the first end and the second end comprising a fluid and a pressure source. At least one of the pressure compartments is filled with a fluid comprising an ink, and when a second end of a pressurized compartment is selected, the piercing tube adjacent to the selected pressurized compartment penetrates the first end of the pressurized compartment causing fluid to flow from the pressurized compartment to the fluid dispenser and in to the fluid connection. Additionally, the tattooing apparatus comprises a pumping mechanism coupled to the fluid connection and adapted to further force the flow of fluid from the fluid dispenser through the fluid connection and to controllably release fluid near the operating end of the tattooing needle. The tattooing apparatus also comprises an adjustable tip coupled to the operating end of the frame and configured to expose a user-selected portion of the tattooing needle.

The invention may further comprise a source of cleansing solution coupled to fluid dispenser. Additionally or alternatively, the invention may house the cleansing solution within at least one of the pressurized compartments.

The motor of the invention may be pneumatic, among other things.

The invention may comprise pressurized compartments that are refillable.

The invention may further comprise a housing coupled to the frame configured to substantially cover the reciprocating armature, the tattooing needle, the fluid connection and the pumping mechanism.

The invention may comprise a cartridge clip coupled to the frame comprising a plurality of compartment openings configured to accept the plurality of pressurized compartments, each comprising a button disposed adjacent to the pressurized compartment; and a release mechanism configured to quickly decouple the cartridge clip from the frame.

The invention may further comprise a valve coupled to each piercing tube.

The invention may further comprise a mixing mechanism in communication with the liquid dispenser.

The invention also comprises a tattooing apparatus comprising a housing with a portion configured to be held in a hand of a user. The apparatus further comprises a frame with an operating end and a distal end adapted to receive a motor, a fluid dispenser, and a reciprocating tattooing needle coupled to the motor. The tattooing needle comprises an operating end extending beyond the operating end of the frame and at least one fluid pathway coupled to the fluid dispenser and disposed near the operating end of the tattooing needle.

In addition, the tattooing apparatus comprises a plurality of piercing tubes each coupled to the fluid dispenser and a plurality of pressurized compartments comprising: a first end disposed adjacent to a piercing tube and comprising a self-sealing fluid-tight seal, a second end configured to be selected, and a reservoir coupled between the first end and the second end comprising a fluid and a pressure source. At least one of the pressure compartments is filled with a fluid comprising an ink, and when a second end of a pressurized compartment is selected, the piercing tube adjacent to the selected pressurized compartment penetrates the first end of the pressurized compartment causing fluid to flow from the pressurized compartment to the fluid dispenser and in to the fluid connection. Additionally, the tattooing apparatus comprises a pumping mechanism coupled to the fluid connection and adapted to further force the flow of fluid from the fluid dispenser through the fluid connection and to controllably release fluid near the operating end of the tattooing needle. The tattooing apparatus also comprises an adjustable tip coupled to the operating end of the frame and configured to expose a user-selected portion of the tattooing needle.

The invention also comprises a method of using a handheld tattooing apparatus comprising the steps of providing a housing with a portion configured to be held in a hand of a user, providing a frame comprising an operating end and a distal end adapted to receive a motor, and providing a fluid dispenser. The method also comprises the steps of providing a reciprocating tattooing needle coupled to the motor and comprising an operating end extending beyond the operating end of the frame, and at least one fluid pathway coupled to the fluid dispenser and disposed near the operating end of the tattooing needle.

The method further comprises the steps of providing a plurality of piercing tubes each coupled to the fluid dispenser, providing a plurality of pressurized compartments comprising a first end disposed adjacent to a piercing tube and comprising a self-sealing fluid-tight seal, a second end configured to be selected, and a reservoir coupled between the first end and the second end and comprising a fluid and a pressure source, and providing a least one pressurized compartment with a fluid comprising an ink. Additionally, the method comprises the step of selecting at least one of the second ends of a pressurized compartment causing the piercing tube adjacent to the selected pressurized compartment to penetrate the first end of the pressurized compartment and in turn causing fluid to flow from the pressurized compartment to the fluid dispenser and in to the fluid pathway. Another step of the method is providing a pumping mechanism coupled to the fluid pathway and further forcing the flow of fluid from the fluid dispenser through the fluid pathway and controllably releasing fluid near the operating end of the tattooing needle with the pumping mechanism. The method also comprises the steps of applying ink to a surface, providing a cleaning solution course coupled to the fluid dispenser, simultaneously feeding the cleaning solution through the fluid dispenser and out of the fluid pathway following an application of ink using the tattooing apparatus, providing an adjustable tip coupled to the operating end of the frame and covering a portion of the tattooing needle, and optionally adjusting the tip to expose a user defined portion of the tattooing needle.

The method may also have the source of cleaning solution be from at least one of the pressurized compartments.

The method may further comprise the step of providing a mixing mechanism in user engageable communication with the fluid dispenser, and engaging the mixing mechanism when more than one pressurized compartment is selected.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographer, to use only the plain and ordinary meaning of terms in the specification and claims unless he clearly states otherwise and then further, expressly sets forth the "special" definition of that term and explains how it differs from the plain and ordinary meaning Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of 35 U.S.C. §112(f). Thus, the use of the words "function," "means" or "step" in the Detailed Description or Description of the Drawings or claims is not intended to somehow indicate a desire to invoke the special provisions of 35 U.S.C. §112(f) to define the invention. To the contrary, if the provisions of 35 U.S.C. §112(f) are sought to be invoked to define the inventions, the claims will specifically and expressly state the exact phrases "means for" or "step for, and will also recite the word "function" (i.e., will state "means for performing the function of injecting ink into a patient's skin"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventor not to invoke the provisions of 35 U.S.C. §112(f). Moreover, even if the provisions of 35 U.S.C. §112(f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

The foregoing and other aspects, features, and advantages will be apparent to those artisans of ordinary skill in the art from the DETAILED DESCRIPTION, DRAWINGS, and CLAIMS.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

FIG. 6 depicts a side view of the fluid dispenser, fluid connection, mixing mechanism and pumping mechanism according to an embodiment of the invention.

FIG. 7 depicts a side view of the fluid dispenser, fluid connection and pumping mechanism including the operation of the pumping mechanism according to an embodiment of the invention.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. The full scope of the inventions is not limited to the examples that are described below.

Figure 1:
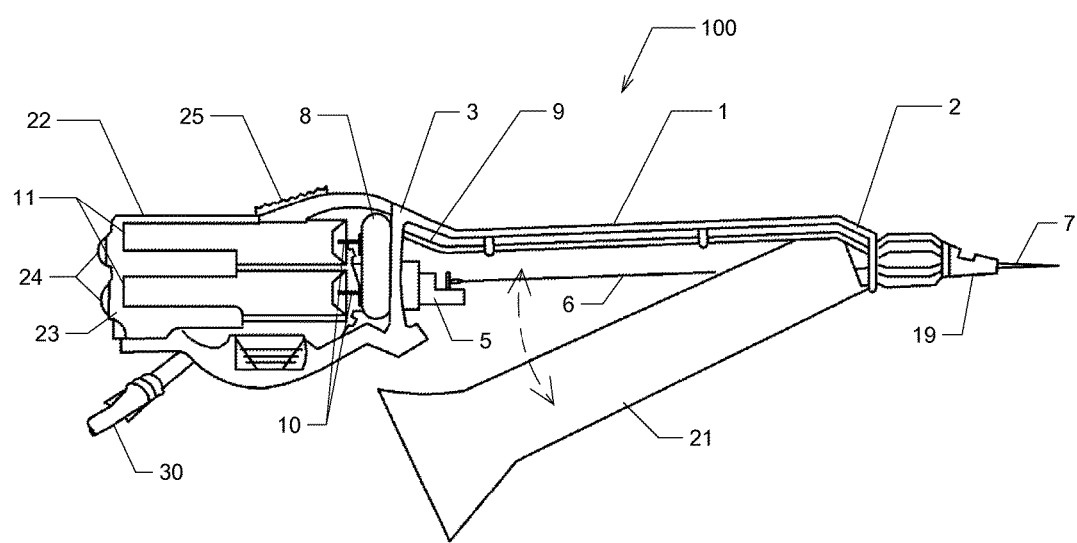
FIG. 1 depicts a side view of the tattooing apparatus according to an embodiment of the invention.

FIG. 1 depicts a side view of an implementation of a tattooing apparatus 100. In some embodiments the tattooing apparatus 100 may comprise a frame 1 with an operating end 2 and a distal end 3 adapted to receive a motor 4. The frame 1 may be constructed of any rigid or semi-rigid material capable of holding the weight of several components described below. In some embodiments it may be preferred to construct the frame 1 of durable, strong and deformable materials that do not rust and that are easily cleaned and sterilized. In such embodiments, examples of exemplary materials may include stainless steel or equivalent materials. In other embodiments, it may be preferred to construct the frame 1 of low-cost disposable material. In these embodiments, the materials may include plastics and other polymers.

Figure 5:
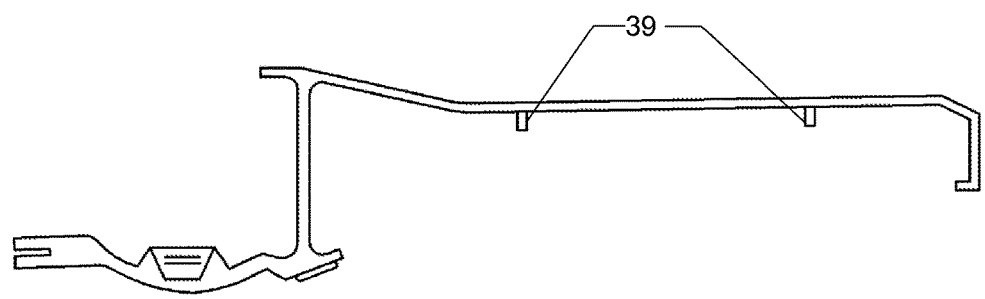
FIG. 5 depicts a side view of part of the frame according to an embodiment of the invention.

In some embodiments, the motor 4 may be mounted to the frame 1 by sliding it into the distal end 3 and snapping it into place. In such an embodiment, the frame 1, as shown in FIG. 5, may include notches, cuts or other attachment portions that accommodate certain motors. In other embodiments, the frame 1 may accommodate a variety of different motors sizes by, for example, adjusting the size of the distal end 3.

In some embodiments, the motor 4 may be pneumatic. If a pneumatic motor 4 is used, there may be an external air source 30, such as an electric air compressor, that connects to the motor 4 through air tubing 38. In other embodiments using a pneumatic motor 4, the air source 30 may be attached and contained on the tattooing apparatus 100. For instance, the air source 30 may be a battery-powered air compressor and may attach to the frame 1 in a similar manner as the motor 4. In other embodiments the motor 4 may be battery-powered, solar-powered, or electric, to name a few examples.

Figure 2:
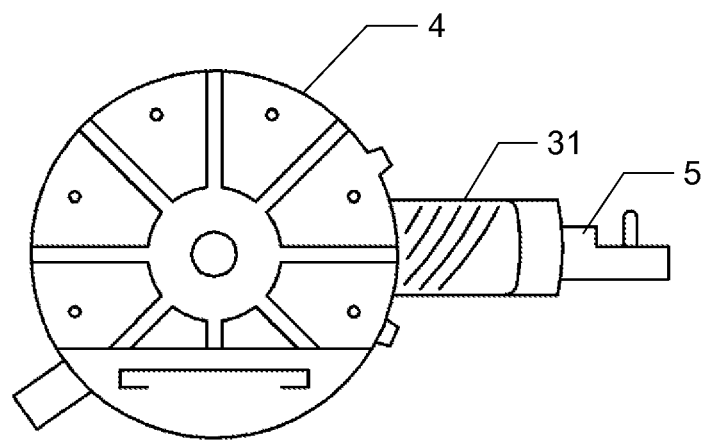
FIG. 2 depicts a side view of the reciprocating armature coupled to the motor according to an embodiment of the invention.

FIG. 2 depicts a side view of exemplary embodiments of the motor 4 comprising a piston 31. An armature 5 may be coupled to the motor 4 in some embodiments. In these embodiments, the motor 4 may move the armature 5 in a reciprocating motion when the motor 4 is turned on. The motor 4 and the armature 5 may be a single unit in some embodiments. In other embodiments the armature 5 may be separate from the motor 4, and attach to the motor 4 in any number of ways, such as through a threaded connection, a hook connection, or no connection at all, whereby a reciprocating piston 31 of the motor 4 abuts one end of the armature 5 causing it to reciprocate. In other embodiments, the piston 31 may act as the reciprocating armature 5.

Figure 3:
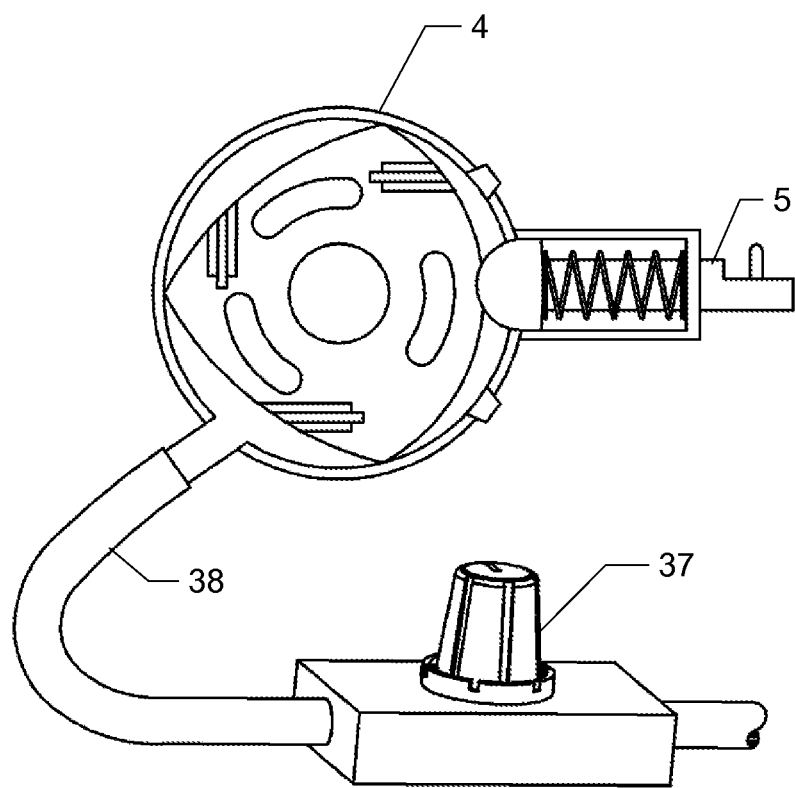
FIG. 3 depicts a side view of the reciprocating armature coupled to a pneumatic motor, which is coupled to a controllable air source according to an embodiment of the invention.

FIG. 3. depicts a side view of a pneumatic motor 4. In some embodiments, there may be an external air source 30, as described above. The external air source 30 may comprise a flow control 37 and air tubing 38 that supplies air to the motor 4, causing the piston 31 to reciprocate.

Referring again to FIG. 1, in some embodiments a tattooing needle 6 may be coupled to the armature 5. In such embodiments, the reciprocating motion of the armature 5 may cause the tattooing needle 6 to reciprocate. The tattooing needle 6 may be detachably connected to the armature 5 by, for example, a screw connection, a plug-in or a clamp connection, or a hook connection. In other embodiments the motor 4 may attach directly to the tattooing needle 6.

The tattooing needle 6 may comprise an operating end 7 extending beyond the operating end 2 of the frame 1. The tattooing needle 6 is adapted to pierce the skin of patients in order to inject ink. The tattooing needle 6 may comprise several needles, as is typical and well known in the art of tattooing.

Still referring to FIG. 1, a fluid dispenser 8 may be coupled to the tattooing apparatus 100. In some embodiments the fluid dispenser 8 may be removably attached to the frame 1 by notches, screws, clamps, snaps, or in many other ways. In other embodiments the fluid dispenser 8 may be removably attached to the motor 4. In some embodiments the fluid dispenser 8 may be shaped such that the ends of the fluid dispenser 8 and the motor 4 that are closest to the operating end 2 of the frame 1 are approximately aligned. In such embodiments, the fluid dispenser may be U-shaped and situated around the motor 4, around the armature, or around the piston 31 of the motor 4, as partially depicted in FIGS. 6 and 7. In other embodiments, the fluid dispenser 8 may be behind, below, in front of, on top of, adjacent to, or apart from the motor 4. In some preferred embodiments the fluid dispenser 8 may be shaped and positioned in a manner that maximizes the use of space thereby minimizing unused areas. The fluid dispenser 8 may also include several points of connection for the introduction, mixing, and/or passing of various fluids 16, including ink 29 for tattooing, as more fully described below. In some embodiments, the connection points may include a male end configured to connect with a female end, or vice versa. In some embodiments, connections may be achieved through threaded connections, flange connections, glued connections, slip-on connections, or in many other ways.

FIGS. 1, 4, 6 and 7 depict views of some embodiments in which a fluid connection 9 may be coupled to the fluid dispenser 8. The fluid connection 9 may comprise flexible, rigid, or semi-rigid tubing, for example. The fluid connection 9 acts as a conduit or channel to transport fluid 16 from the fluid dispenser 8 to the operating end 7 of the tattooing needle 6. The fluid connection 9 may be attached anywhere on the fluid dispenser 8.

FIG. 5 depicts a side view of the frame 1. In some embodiments, the fluid connection 9 may be supported along the length of the frame 1 by one or more supports 39. Such supports 39, may include, for example, brackets, rings, straps, or any other support capable of holding the fluid connection 9 in place along the length of the frame 1. In some embodiments, the fluid connection 9 may comprise multiple pathways or conduits that transport fluid 16 to the operating end 7. In other embodiments, the tattooing needle 6 may be the fluid connection 9. In these embodiments, the tattooing needle 6 may comprise one or more pathways contained within the tattooing needle 6 that run the length of the needle.

FIGS. 6 and 7 depict side views of the fluid dispenser 8 as used in some embodiments. As shown, the fluid dispenser is some embodiments may comprise two or more separate pieces that connect together to form a volume capable of containing fluid 16. In some embodiments, a pumping mechanism 18 may be coupled to the fluid connection 9. The pumping mechanism 18 may comprise a valve that prevents the passage of fluid 16 until actuated by a user. The pumping mechanism 18 may comprise a mechanical or electrical unit that pulls fluid 16 from the fluid dispenser 8 and/or from the fluid connection 9, and releases it near the operating end 7 of the tattooing needle 6.

The liquid dispenser 8 may have a plurality of piercing tubes 10 coupled to it. The piercing tubes 10 may be attached to the liquid dispenser 8 in numerous ways, such as through threading, welding, flanges, or manufactured as an integrated unit with the liquid dispenser 8. In some embodiments a valve 32 may be coupled to some or all of the piercing tubes 10. In some embodiments the connection of the piercing tubes 10 to the fluid dispenser 8 may be reinforced by a support structure 26, such as a built up material around the piercing tube 10. One end of the piercing tubes 10 may be open to the air and the other end may open up into the liquid dispenser 8, or the other end may connect to a valve 32, as described above, and when the valve 32 is in an open position, it opens up into the liquid dispenser 8.

In some embodiments, at least two pressurized compartments 11 may be removably attached to the tattooing apparatus 100. Each pressurized compartment 11 may comprise a first end 12 disposed adjacent to one of the piercing tubes 10, a second end 14 configured to be selected or engaged by a user, and a reservoir 15. In some embodiments the first end may be disposed adjacent to several piercing tubes 10. In other embodiments, the first end may be centered over a piercing tube 10, such that the piercing tube 10 is aimed at roughly the center of the pressurized compartment 11.

In some embodiments, the first end 12 may comprise a self-sealing fluid-tight seal 13. The second end 14 may be sufficiently firm to be pressed by a user with little or no shape deformation. The reservoir 15 may be coupled between the first end 12 and the second end 14 and may comprise a fluid 16 and a pressure source 17. The pressure source 17 in some embodiments may comprise a pressure spring 35 that is connected to and pushes a ring tappet 34 surrounding a disc 33. In some embodiments, at least one of the pressurized compartments 11 may be filled with a fluid 16 comprising ink 29. In some embodiments, all of the compartments 11 may be filled with a fluid comprising ink 29 of one or various colors. In other embodiments, at least one compartment may be filled with a cleaning solution. Some embodiments may use a hepatic cleaning solution that is safe for human use and injection. Other embodiments may use a sterilizing cleaning solution. The cleaning solution should be a clear fluid. Other embodiments may comprise an external source of cleaning solution that is supplied to the fluid dispenser 8 by a cleansing solution tube 20.

In some embodiments, a user may select a pressurized compartment 11 in order to engage it for the tattooing or cleansing process. Engaging a pressurized compartment 11 initiates the process by which ink is supplied to the tattooing needle during the tattooing process. Engaging multiple pressurized compartments may provide a way to mix inks 29 of various colors. Mixing of inks 29 may be achieved by initiating a mixing mechanism 27, which, in some embodiments, may be coupled to or contained within the fluid dispenser 11. Mixing mechanisms 27 may come in several forms; one example is a magnetic spin bar. Engaging a pressurized compartment 11 filled with a cleaning solution may assist in cleaning out the color(s) that the user previously used. For instance, during the tattooing process, the user may wish to change colors from black to red. This may be achieved by disengaging the pressurized compartment 11 filled with black ink; running cleaning solution through the system, by, for example, pulling cleaning solution from an external source, or by engaging a pressurized compartment 11 filled with cleaning solution, using the pumping mechanism to run the cleaning solution through the system until the fluid output is clear; then engaging the pressurized compartment 11 filled with red ink.

Selecting a pressurized compartment 11 may be achieved by pushing the second end 14. In some embodiments, there may be an engaging spring 36 surrounding one, several, or all of the piercing tubes 10. In other embodiments, there may be an engaging spring 36 on the first end 12 of one, several or all of the pressurized compartments 11, or inside one, several, or all of the pressurized compartments 11. In other embodiments, the engaging spring 36 may be located on the second end 14 of one, several or all of the pressurized compartments 11, or on buttons 24 adjacent to the second end 14 of one, several or all of the pressurized compartments 11. Thus, one or more pressurized compartments 11 may be selected by applying force to the second end 14 of the desired pressurized compartment 11, or by applying force to a button 24 adjacent to the second end 14 of the desired pressurized compartment 11. This force causes the engaging spring 36 to engage the selected pressurized compartment 11. The engaging spring 36 may take many forms, and need only hold the selected pressurized compartment 11 in an engaged position.

Figure 4:
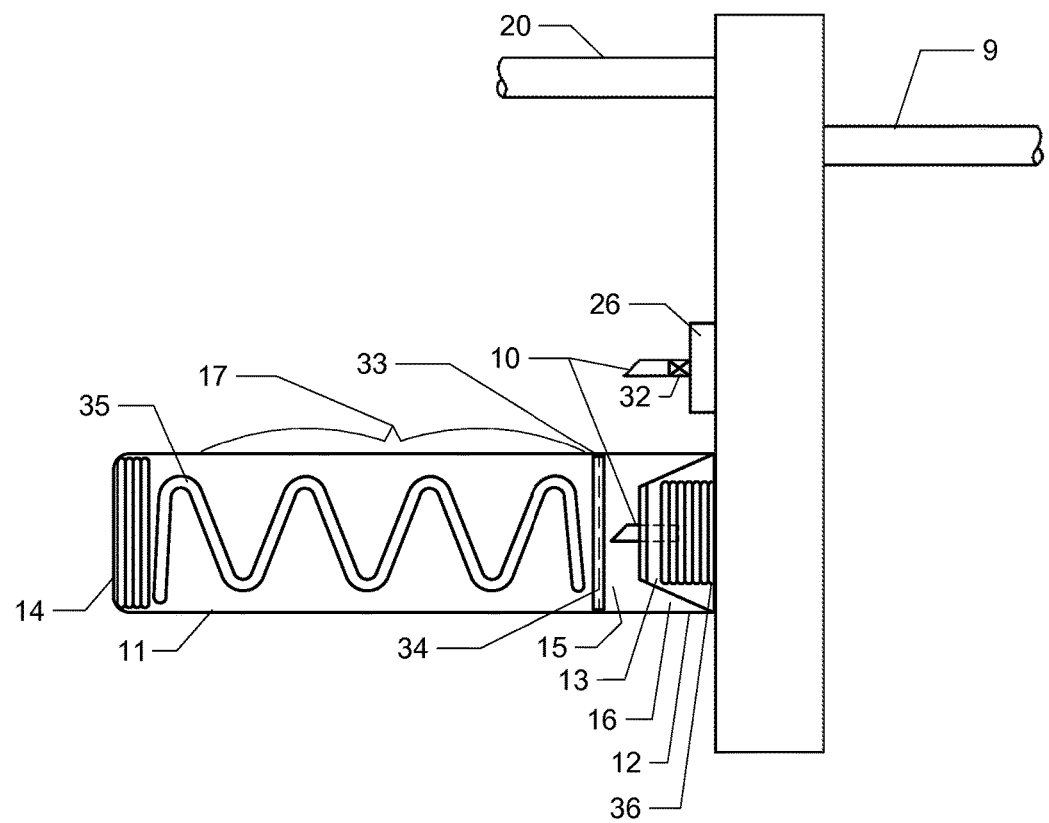
FIG. 4 depicts a side view of the fluid dispenser, the piercing tubes, and one pressurized compartment according to an embodiment of the invention.

FIG. 4 depicts a side view of a pressurized compartment 11 in an engaged position. The engaged position may occur in some embodiments after a user selects at least one pressurized compartment 11, causing the piercing tube 10 adjacent to the selected pressurized compartment 11 to penetrate the first end 12 of the pressurized compartment 11 allowing fluid 16 to flow from the pressurized compartment 11 to the fluid dispenser 8 and into the fluid connection 9. When the user is ready to apply ink 29 to a patient's skin, the user may activate the pumping mechanism 18, which further forces fluid 16 to flow from the fluid dispenser 8 through the fluid connection 9. Moreover, the pumping mechanism 18 prevents fluid 16 from flowing beyond the point of the pumping mechanism 18 until activated by the user. Thus, activation of the pumping mechanism 18 provides the user with the ability to control the release of fluid 16 at desired quantities. Fluid 16 is released near the operating end 7 of the tattooing needle 6.

When a pressurized compartment 11 is filled with fluid 16, the pressure spring 35 may be compressed with the disc 33 and ring tappet 34 being located near the second end 14 of the pressurized compartment 11. Once a pressurized compartment 11 is engaged, the self-sealing fluid-tight seal may be penetrated by a piercing tube 10, as described above, causing fluid 16 to flow from the pressurized compartment 11. Upon penetration, the pressure spring 35 continues to force fluid 16 to flow through the piercing tube 10, into the fluid dispenser 8, through the fluid connection 9 to the pumping mechanism 18. Disengaging a pressurized compartment 11, by pressing it again, clicks the pressurized compartment 11 back into a starting position, removing the piercing tube 10 from inside the pressurized compartment 11. The self-sealing fluid-tight seal 13 reseals the pressurized compartment 11. The self-sealing fluid-tight seal 13 may be constructed of rubber, polymer, or any other material that is elastic and deformable enough to be pierced and regain fluid containing function.

Figure 8:
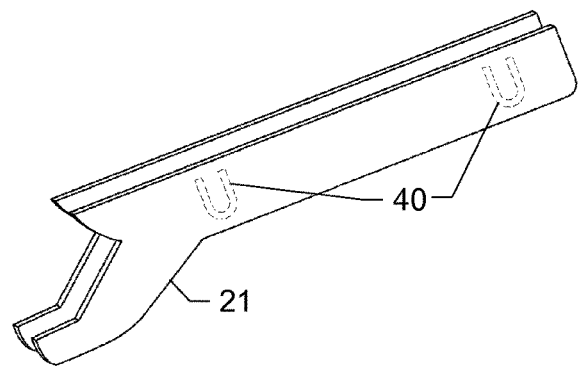
FIG. 8 depicts an isometric view of the housing according to an embodiment of the invention.
Figure 9:
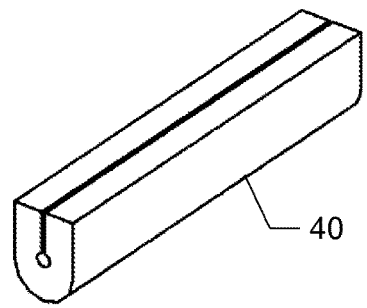
FIG. 9 depicts an isometric view of a portion of the inside of the housing according to an embodiment of the invention.

FIG. 8 depicts an isometric view of a housing 21, as used in some embodiments. The tattooing apparatus 100 may comprise a housing 21, which is removably coupled to the frame 1. The housing 21 may be adapted to be held in a hand of a user. The housing 21 may come in various sizes to accommodate various users. In a shut position, the housing 21 may substantially cover the armature 5, the tattooing needle 6, the fluid connection 8, and the pumping mechanism 18. FIG. 9 depicts an isometric interior view of a portion of the housing 21 comprising a guide 40. The guide 40 may comprise a slit, cut, channel, or other passageway that surrounds either the tattooing needle 6 or the fluid connection 9, or both.

Figure 10:
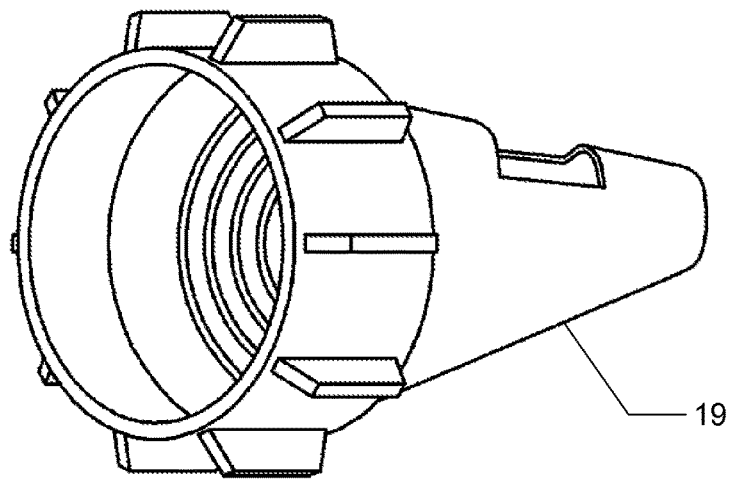
FIG. 10 depicts an isometric view of the adjustable tip according to an embodiment of the invention.

FIG. 10 depicts an isometric view of an adjustable tip 19. The tattooing apparatus 100 may further comprise the adjustable tip 19 in some embodiments, shown in FIG. 1. The adjustable tip 19 may be coupled to the operating end 2 of the frame 1 and configured to expose a user-selected portion of the tattooing needle 6.

Figure 11:
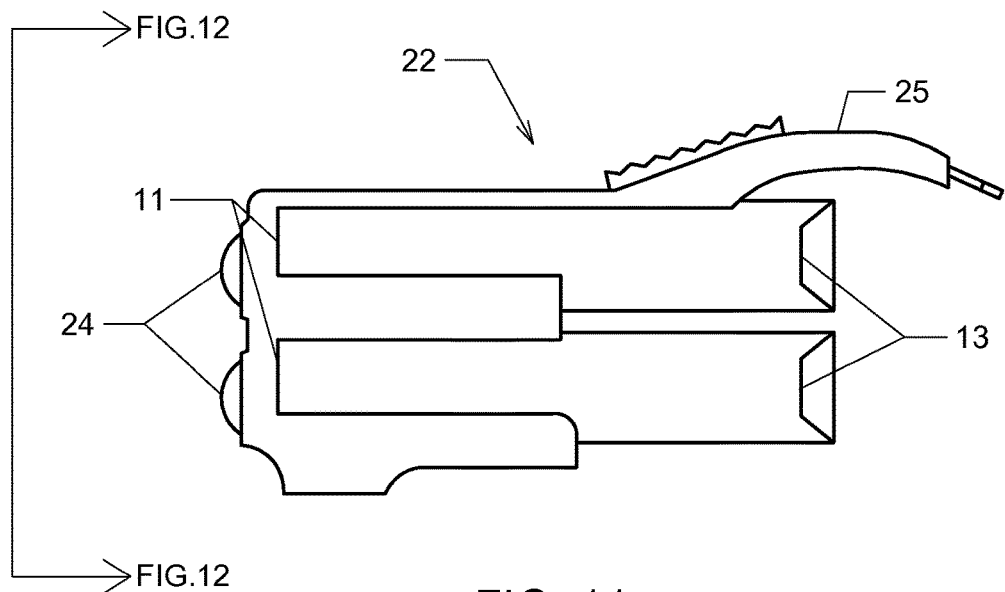
FIG. 11 depicts a side view of the ink cartridge clip.
Figure 12:
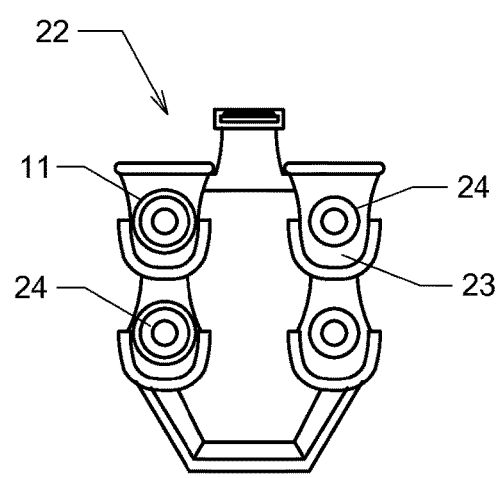
FIG. 12 depicts a rear view of the ink cartridge clip.

FIG. 11 depicts a side view of a cartridge clip 22 and FIG. 12 depicts a rear view of the cartridge clip 22. The pressurized compartments 11 may be contained within the cartridge clip 22. The cartridge clip 22 may comprise compartment openings 23 in which pressurized compartments 11 are placed. The cartridge clip 22 may also include buttons 24 disposed adjacent to the second end 14. A user may press a button 24 to engage or select a chosen pressurized compartment 11. In addition, the cartridge clip 22 may include a release mechanism 25, which allows a user to quickly remove and replace a cartridge clip 22, or to remove a cartridge clip 22 in order to insert pressurized compartments 11 into the compartment openings 23.

In some embodiments the positioning, shape, alignment or overall configuration of the components of the overall tattooing apparatus 100 may be balanced, meaning that the frame 1 and many or all of the components that attach thereto may be symmetrical and positioned along a common axis in order to evenly distribute weight and shape. The goal may be to create a device that imitates the feel (albeit heavier) of using a pen, pencil, or other instrument used by artists to create designs.

I claim:

1. A tattooing apparatus comprising:
a housing coupled to a frame,
wherein the housing comprises a shutting mechanism configured to cover the frame,
and the frame comprises an operating end and a distal end adapted to receive a motor,
wherein the motor is coupled to a reciprocating piston configured to oscillate an armature of a tattooing needle, the tattooing needle coupled to the reciprocating piston and comprising:
an operating end extending beyond the operating end of the frame;
and at least one fluid pathway coupled to the fluid dispenser and disposed near the operating end of the tattooing needle;
a fluid dispenser comprising:
a plurality of connection points configured to mix, pass, and introduce a plurality of fluids;
a plurality of pressurized compartments comprising:
a resealing first end disposed adjacent to a piercing tube and comprising a self-sealing fluid-tight seal configured to reseal the pressurized compartment;
an enclosed second end configured to be selected; and
a reservoir coupled between the resealing first end and the enclosed second end and comprising a fluid and a pressure source, wherein the reservoir is configured to be refilled with a fluid,
a plurality of piercing tubes each coupled to the fluid dispenser,
wherein at least one piercing tube is configured to penetrate at least one of the plurality of pressurized compartment,
wherein at least one pressurized compartment is filled with a fluid comprising an ink;
wherein when at least one of the enclosed second ends of a pressurized compartment is selected, the piercing tube adjacent to the selected pressurized compartment penetrates the resealing first end of the pressurized compartment causing fluid to flow from the pressurized compartment in to the fluid dispenser and in to the fluid pathway; and
a pumping mechanism coupled to a valve coupled to the fluid pathway and adapted to further force the flow of fluid from the fluid dispenser through the fluid pathway and to controllably release fluid near the operating end of the tattooing needle, and a removable adjustable tip coupled to the operating end of the frame and configured to expose a user selected portion of the tattooing needle.

2. The tattooing apparatus of claim 1, further comprising a source of cleansing solution coupled to the fluid dispenser.

3. The tattooing apparatus of claim 2, wherein the source of cleansing solution is from at least one of the pressurized compartments.

4. The tattooing apparatus of claim 1, wherein the motor is pneumatic.

5. The tattooing apparatus of claim 1, wherein the pressurized compartments are refillable.

6. The tattooing apparatus of claim 1, wherein the reciprocating tattooing needle, the fluid dispenser, the housing, the pumping mechanism, and the adjustable tip are disposable.

7. The tattooing apparatus of claim 1, further comprising a mixing mechanism in communication with the fluid dispenser.

* * * * *